United States Patent
Genoud et al.

(10) Patent No.: US 9,222,470 B2
(45) Date of Patent: Dec. 29, 2015

(54) MICROPUMP

(75) Inventors: Dominique Genoud, Kaltbrunn (CH);
Peter Christen, Obergerlafingen (CH);
Franck Robin, Lenzburg (CH); Helmut Thiemer, Sachseln (CH)

(73) Assignee: SENSILE PAT AG, Haegendorf (CH)

(*) Notice: Subject to any disclaimer, the term of this patent is extended or adjusted under 35 U.S.C. 154(b) by 495 days.

(21) Appl. No.: 13/635,010

(22) PCT Filed: Mar. 15, 2011

(86) PCT No.: PCT/IB2011/051071
§ 371 (c)(1),
(2), (4) Date: Sep. 14, 2012

(87) PCT Pub. No.: WO2011/114285
PCT Pub. Date: Sep. 22, 2011

(65) Prior Publication Data
US 2013/0017099 A1    Jan. 17, 2013

(30) Foreign Application Priority Data
Mar. 17, 2010 (CH) .................................... 0376/10

(51) Int. Cl.
*F04B 7/06* (2006.01)
*F04B 7/04* (2006.01)
(Continued)

(52) U.S. Cl.
CPC .............. *F04B 7/06* (2013.01); *A61M 5/14216* (2013.01); *A61M 5/16831* (2013.01);
(Continued)

(58) Field of Classification Search
CPC .......... F04D 15/0263; F04B 7/04; F04B 7/06; F04B 7/045; F02M 41/12; F02M 41/121

USPC ............... 417/9, 50, 491, 492, 498, 500;
415/172.1; 137/614.2
See application file for complete search history.

(56) References Cited

U.S. PATENT DOCUMENTS 1,238,939 A * 9/1917 Pfleeger ..................... 417/500
1,866,217 A * 7/1932 Mayer ........................ 417/500
(Continued)

FOREIGN PATENT DOCUMENTS

EP          1527793          5/2005
WO     WO 92/16747          10/1992
(Continued)

OTHER PUBLICATIONS
Written Opinion in International Application No. PCT/IB2011/051071, Oct. 10, 2011, pp. 1-13.

*Primary Examiner* — Alexander Comley
(74) *Attorney, Agent, or Firm* — Saliwanchik, Lloyd & Eisenschenk

(57) ABSTRACT

A pump comprising a housing comprising a rotor chamber, inlet and outlet channels opening into the rotor chamber, and inlet and outlet seals mounted on a surface of the chamber, and a rotor rotatably and axially slidably received in the chamber and comprising a first axial extension comprising a liquid supply channel and a second axial extension comprising a liquid supply channel, the first and second axial extensions having different diameters. The inlet and outlet seals engage a surface of the rotor, whereby the liquid supply channel of each axial extension in conjunction with a corresponding seal forms a valve that opens and closes as a function of the angular and axial displacement of the rotor. At least one of the inlet and outlet channels opens transversely into the rotor chamber and at least one of the inlet and outlet seals forms a closed circuit circumscribing said at least one of the inlet and outlet channels.

13 Claims, 7 Drawing Sheets

(51) Int. Cl.
*A61M 5/142* (2006.01)
*A61M 5/168* (2006.01)
*F04B 9/04* (2006.01)
*F04B 19/00* (2006.01)
*A61M 5/36* (2006.01)

(52) U.S. Cl.
CPC ............... *F04B 7/045* (2013.01); *F04B 9/042* (2013.01); *F04B 9/047* (2013.01); *F04B 19/006* (2013.01); *A61M 5/36* (2013.01); *A61M 2005/16863* (2013.01)

(56) References Cited

U.S. PATENT DOCUMENTS

| | | | | |
|---|---|---|---|---|
| 2,385,089 A * | 9/1945 | Lerner | ...................... | 137/599.12 |
| 3,168,872 A * | 2/1965 | Pinkerton | ...................... | 417/492 |
| 3,256,821 A * | 6/1966 | Brederhoff | ...................... | 417/494 |
| 3,386,383 A * | 6/1968 | Dreher | ...................... | 417/498 |
| 3,447,468 A * | 6/1969 | Kinne | ...................... | 417/403 |
| 4,008,003 A * | 2/1977 | Pinkerton | ...................... | 417/250 |
| 4,067,668 A * | 1/1978 | Nimell | ...................... | 417/492 |
| 4,364,718 A * | 12/1982 | Beun et al. | ...................... | 417/500 |
| 4,536,140 A * | 8/1985 | Guthrie | ...................... | 417/500 |
| 4,553,506 A * | 11/1985 | Bekiaroglou | ...................... | 123/45 R |
| 4,854,837 A * | 8/1989 | Cordray | ...................... | 417/492 |
| 4,883,467 A * | 11/1989 | Franetzki et al. | ...................... | 604/152 |
| 4,941,809 A * | 7/1990 | Pinkerton | ...................... | 417/500 |
| 4,964,533 A * | 10/1990 | Allington et al. | ...................... | 222/14 |
| 5,074,767 A * | 12/1991 | Gerlach et al. | ...................... | 417/500 |
| 5,312,233 A * | 5/1994 | Tanny et al. | ...................... | 417/316 |
| 5,494,420 A * | 2/1996 | Mawhirt et al. | ...................... | 417/500 |
| 5,601,421 A * | 2/1997 | Lee | ...................... | 417/492 |
| 5,961,303 A * | 10/1999 | King | ...................... | 417/492 |
| 6,506,033 B2 * | 1/2003 | Fukami | ...................... | 417/420 |
| 7,159,507 B2 * | 1/2007 | Grollimund et al. | ...................... | 92/31 |
| 7,384,249 B2 * | 6/2008 | Romanin | ...................... | 417/469 |
| 7,726,955 B2 * | 6/2010 | Ryser et al. | ...................... | 417/420 |
| 7,798,783 B2 * | 9/2010 | Burns et al. | ...................... | 417/53 |
| 8,282,366 B2 * | 10/2012 | Hilber et al. | ...................... | 417/420 |
| 2004/0101426 A1 * | 5/2004 | Wahlberg | ...................... | 417/492 |
| 2007/0071596 A1 * | 3/2007 | Ryser et al. | ...................... | 415/172.1 |
| 2009/0123309 A1 * | 5/2009 | Hilber et al. | ...................... | 417/417 |

FOREIGN PATENT DOCUMENTS

| | | | |
|---|---|---|---|
| WO | WO 9216747 A1 * | 10/1992 | |
| WO | WO 2005/039674 | 5/2005 | |
| WO | WO 2007/074363 | 7/2007 | |
| WO | WO 2007074363 A2 * | 7/2007 | |

* cited by examiner

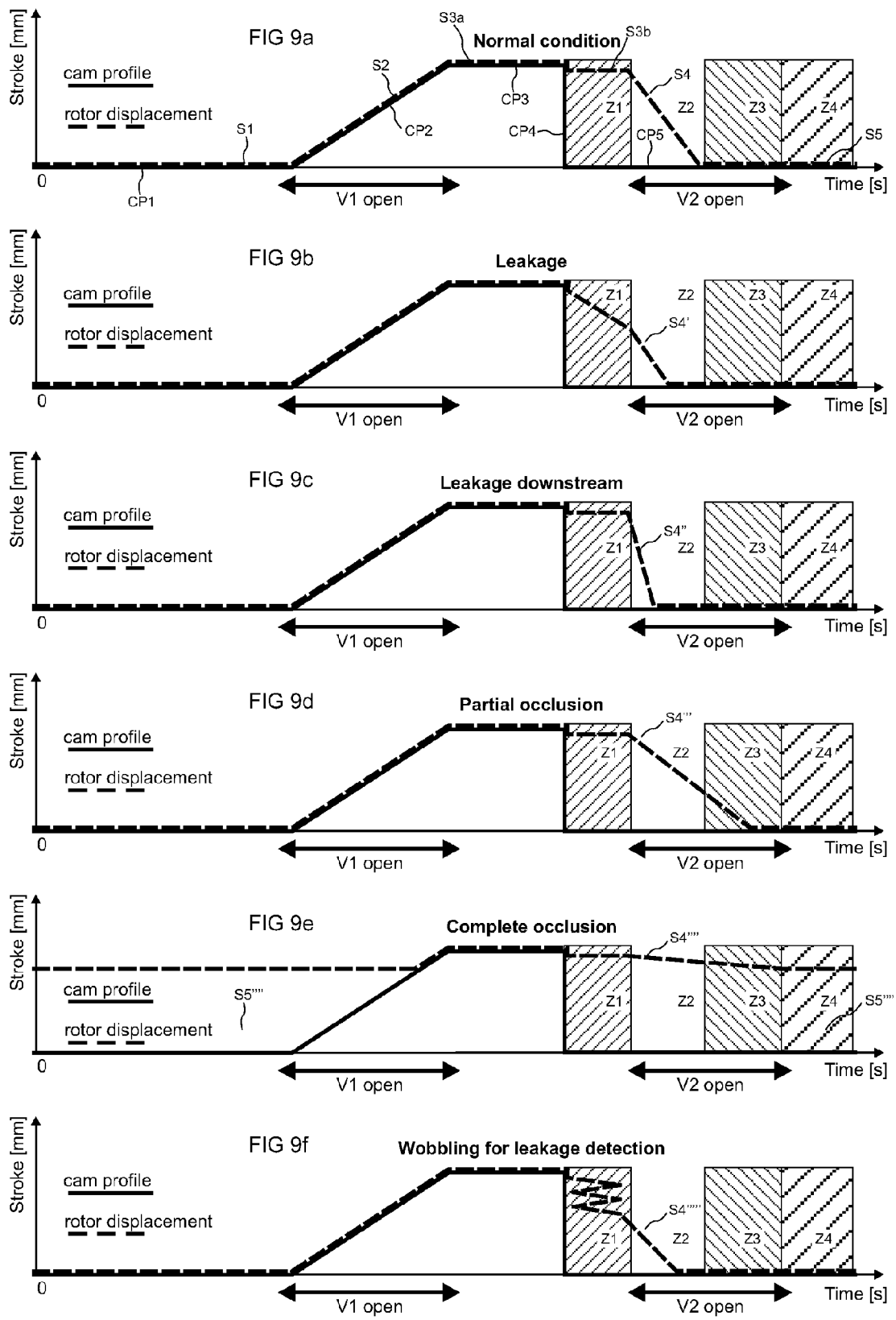

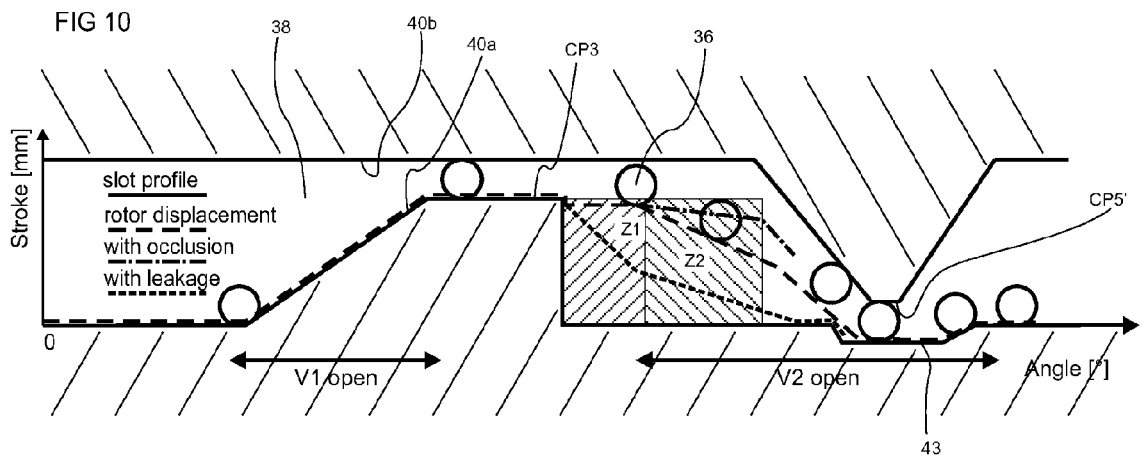
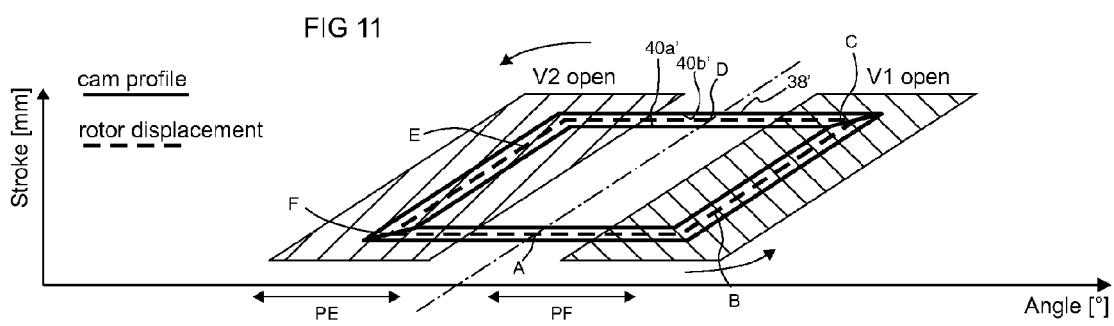

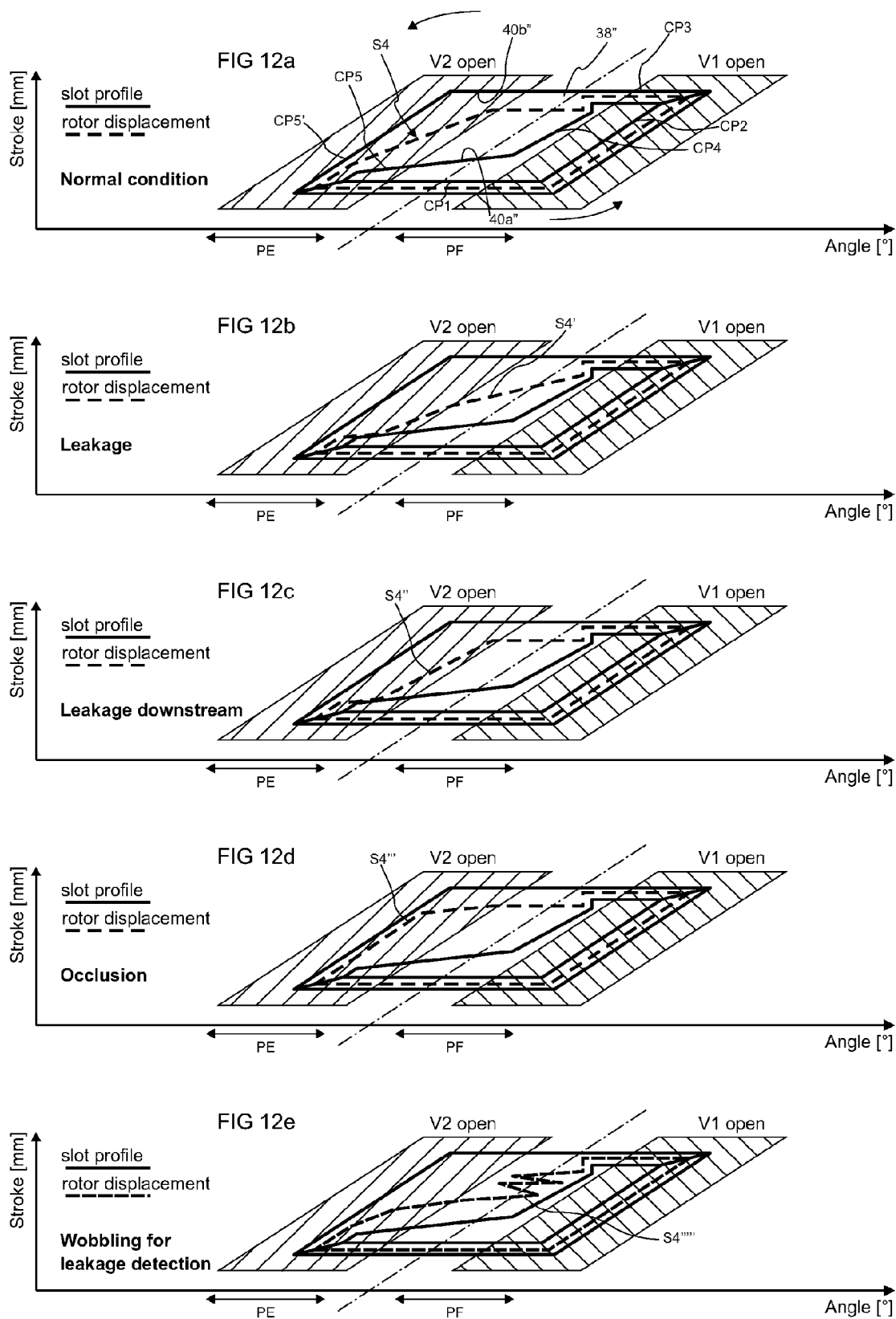

MICROPUMP

CROSS-REFERENCE TO RELATED APPLICATION

This application is the U.S. national stage application of International Patent Application No. PCT/IB2011/051071, filed Mar. 15, 2011, the disclosure of which is hereby incorporated by reference in its entirety, including all figures, tables and amino acid or nucleic acid sequences.

The present invention relates to a micropump with a rotatably and axially movable rotor. The micropump may be used, inter alia, in medical applications for the administration of drugs, in non-medical applications or for diagnostic purposes.

A micropump for precise administration of small quantities of a liquid or pasty liquid is described in international applications WO2005039674 and WO2007074363. The rotational and axial movement of the rotor relative to the housing creates a pumping action while opening and closing valves to draw liquid into the pump and to expel liquid from the pump. A curve on the rotor cooperating with a complementary cam on the housing causes the axial displacement of the rotor when one of the valves is open. When both valves are closed, axial displacement of the rotor should be essentially nil subject to a certain elasticity of the chamber containing the liquid, the liquid being essentially incompressible. The presence of air in the pump or of occlusions hindering the flow of the liquid downstream of the pump may affect the axial displacement of the rotor and the pumping characteristics of the pump.

In many medical applications, such as the transcutaneous or intravenous delivery of liquid drugs, the presence of air in the liquid to be administered is highly undesirable. In drug delivery systems there may also be occurrences of occlusion, for example due to blood clotting or crushing of catheter tubing or more generally application or build-up of a back-pressure, or of leakage. In many conventional systems, separate pressure sensors are installed in the system with a view of detecting occlusion or leakage however such systems are usually not adapted to detect reliably air bubbles. Moreover, the presence of separate sensors complicates the pump system and renders it more complex and costly to operate. The pump and pressure sensors being separate, there is also a certain risk that the sensors may function incorrectly without being noticed without discontinuing the operation of the pump.

The detection of occlusion or leakage of a pump system, or the detection of presence of air in a pump would also be useful in many applications outside the medical field.

In many applications it is desirable to have an economical disposable pump system that is able to pump small quantities of liquid accurately, safely and reliably, in particular for single or limited use pump applications. Such applications may include for instance pumps of portable drug delivery systems such as insulin patch pumps, liquid dosing systems in laboratory or consumer applications, print cartridges, and many other applications.

An object of this invention is to provide a pump for that is accurate, reliable, compact, and economical to manufacture.

It would be advantageous to provide a micropump that is particularly cost effective to manufacture, such that it could be provided as a disposable system.

It would be advantageous to provide a pump with reliable means for detecting occlusion or leakage in the pump or downstream or upstream of the pump.

It is another object of this invention to provide a disposable micropump for medical applications that is economical, reliable and safe and that can deliver small quantities of liquid very accurately.

Objects of this invention have been achieved by providing a pump according to the present invention.

Other objects of this invention have been achieved by providing a method of detecting leakage or occlusion.

Disclosed herein is a pump comprising a housing, comprising a rotor chamber, inlet and outlet channels opening into the rotor chamber, and inlet and outlet seals mounted on a surface of the chamber, and a rotor rotatably and axially slidably received in the chamber and comprising a first axial extension comprising a liquid supply channel and a second axial extension comprising a liquid supply channel, the first and second axial extensions having different diameters. The inlet and outlet seals engage a surface of the rotor, whereby the liquid supply channel of each axial extension in conjunction with a corresponding seal forms a valve that opens and closes as a function of the angular and axial displacement of the rotor. At least one of the inlet and outlet channels opens transversely or radially into the rotor chamber and at least one of the inlet and outlet seals forms a closed circuit circumscribing said at least one of the inlet and outlet channels.

In an advantageous embodiment, both inlet and outlet channels open transversely into the rotor chamber and both inlet and outlet seals each forms a closed circuit circumscribing respective inlet and outlet channels. The surface circumscribed by either the inlet or the outlet seal preferably wraps around the corresponding rotor extension over an angle ($\alpha$, $\beta$) less than 180°.

In an embodiment, the rotor is configured to oscillate over a rotation angle less than 360°, a back and forth movement constituting a pumping cycle.

In another embodiment, the rotor is configured to rotate in a single direction, a rotation angle of 360° constituting a pumping cycle.

The rotor and housing may comprise inter-engaging cam elements to effect the rotor axial displacement as a function of the rotation angle. In an advantageous variant, said cam elements comprising a double sided cam slot. The double sided cam slot may have a varying width in a variant configured to enable leakage or occlusion detection.

In the non oscillating variant, the axial displacement during pump filling may be defined by a cam section on one side of the cam slot, and the axial displacement during pump expelling defined by a cam section on an opposite side of the cam slot, the opposing cam surfaces acting as reference surfaces that accurately define the volume of pumped liquid at each cycle.

In an oscillating variant, the cam slot comprises a first portion defining the axial displacement in one rotation direction, and a second portion defining the axial displacement in an opposite rotation direction. At a transition position in the cam slot corresponding to a change in direction of rotation, the cam slot may advantageously comprises a step down or a point of no return configured to ensure that a complementary cam finger progresses from one cam slot portion to the other cam slot portion.

Also disclosed herein is a method of detecting occlusion or leakage of a pump, including the steps of performing an initial measurement comprising turning the rotor in a forward pumping direction at least one revolution and storing the axial displacement as a function of rotation displacement profile in a look-up table as a cam profile, measuring the rotor axial displacement as a function of rotation displacement during subsequent pumping and comparing the measured rotor displacement with the stored cam profile.

Before the cam profile setting, the rotor may be rotated in a reverse direction until a cam shoulder abuts a complementary cam finger, thus setting a defined reference starting position.

In an advantageous variant, a back and forth displacement of the rotor may be effected over an angle less than 90° when both valves V1 and V2 are closed to detect leakage.

Also disclosed herein is a method of removing gas bubbles or detecting leakage in a pump comprising a housing portion and an axially and rotatably movable rotor portion mounted in the housing portion and having an inlet valve (V1) and an outlet valve (V2), the method including applying a back and forth displacement of the rotor over an angle less than 180° while applying an axial force on the rotor. The back and forth displacement of the rotor occurs when both valves (V1, V2) are closed, preferably over an angle less than 90°.

A pump disclosed herein may in particular be adapted for medical applications, including for the administration of liquid medicaments.

Further objects and advantageous aspects of the invention will be apparent from the claims and the following detailed description of an embodiment of the invention in conjunction with the drawings in which:

FIG. 1a is a cross-sectional view of a pump module according to an embodiment of the invention;

FIGS. 1b and 1c are exploded perspective views of the module of FIG. 1a with the housing illustrated as partially transparent to better view the rotor therein;

FIG. 1d is a cross-sectional view through line 1d-1d of FIG. 1a and FIG. 1e is a cross-sectional view through line 1e-1e of FIG. 1a;

Figure 6:
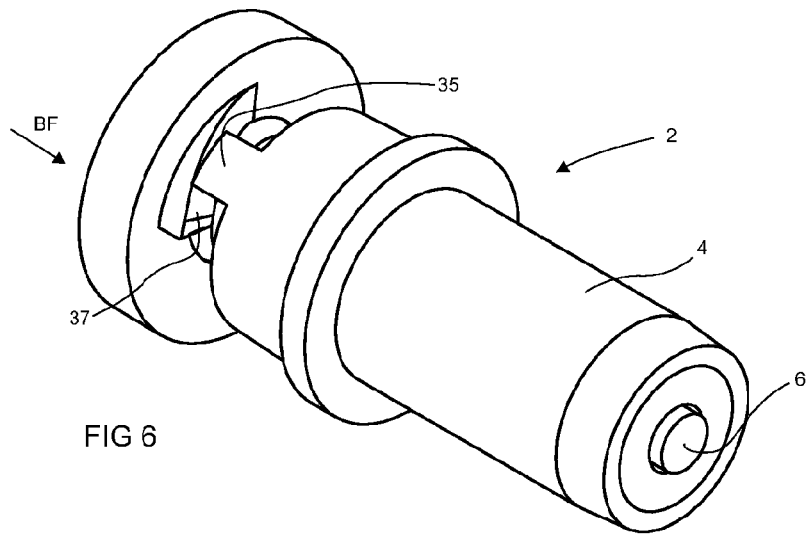
Figure 7:
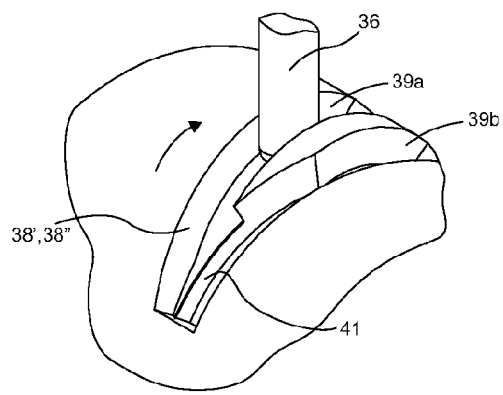
Figure 8:
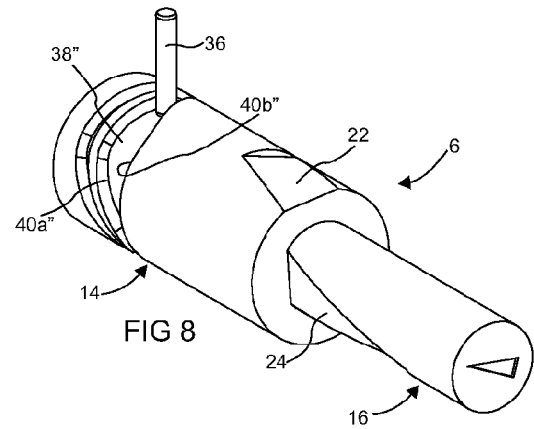

FIGS. 4a to 4f are perspective views of a rotor and housing of a pump module according to an embodiment of the invention, the housing being shown as partially transparent in order to better view the rotor therein, the different views 4a to 4f illustrating different rotational and axial position of the rotor relative to the housing to illustrate the pumping function of this embodiment, which relates to a rotor that rotates less than a full 360° in one direction or the other in an oscillating movement;

FIGS. 5a to 5f are illustrations similar to FIGS. 4a to 4f but of another embodiment of the invention corresponding to a rotor rotating a full 360° in one direction to perform a pumping cycle;

FIG. 6 is a perspective view of a pump module according to a variant with a single sided cam defining the rotor axial movement;

FIG. 7 is a detailed perspective partial view of a double sided cam variant;

FIG. 8 is a perspective view of a rotor with a double sided cam according to a variant of the invention;

FIG. 9a is a graph illustrating the axial displacement (stroke) of the pump rotor as a function of the angular displacement of the rotor for a normal operating condition;

FIG. 9b is a graph similar to FIG. 9a illustrating a leakage condition of the pump;

FIG. 9c is a graph similar to FIG. 9a illustrating a leakage condition downstream of the pump;

FIG. 9d is a graph similar to FIG. 9a illustrating a partial occlusion condition;

FIG. 9e is graph similar to FIG. 9a illustrating a complete occlusion condition;

FIG. 9f is a graph similar to FIG. 9a illustrating a leakage condition of the pump detected by performing a wobbling movement of the rotor;

FIG. 10 is a graph illustrating the axial displacement (stroke) of the pump rotor as a function of the angular displacement of the rotor for a variant with a double sided cam and a rotor displacement of 360° in one direction (embodiment of FIGS. 5a to 5f);

FIG. 11 is a graph illustrating the axial displacement of an oscillating pump rotor with a double sided cam according to an embodiment as a function of the angular displacement of the rotor; and FIGS. 12a-12e are graphs illustrating the axial displacement of an oscillating pump rotor with a double sided variable slot width cam according to an embodiment of the invention that allows detection of leakage or occlusion, where FIG. 12a illustrates a normal condition, FIG. 12b illustrates a leakage condition in the pump, FIG. 12c illustrates a leakage condition downstream of the pump, FIG. 12d illustrates an occlusion condition, and FIG. 12e illustrates a leakage condition of the pump detected by performing a wobbling movement of the rotor.

Figure 1:
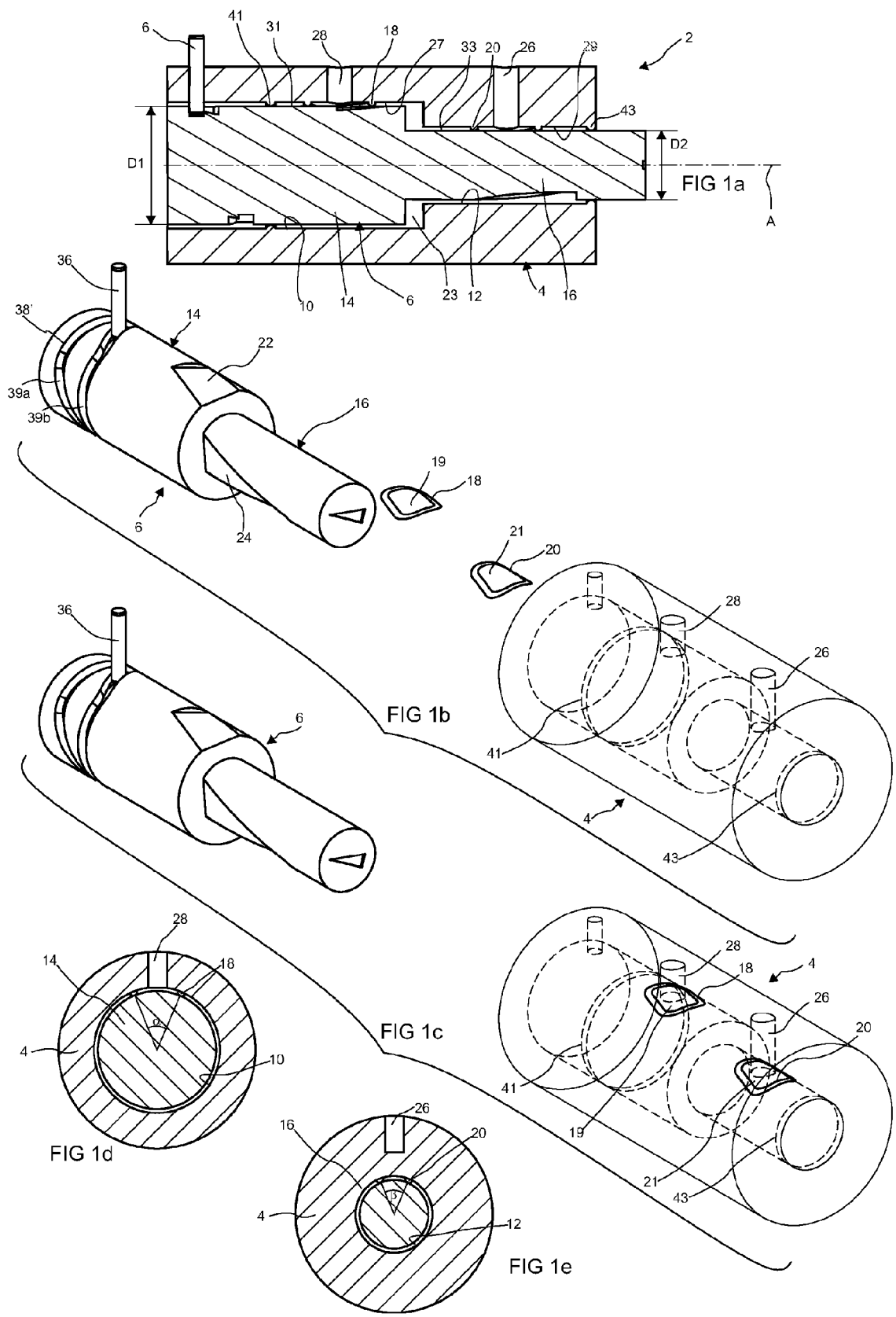

Referring to the figures, in particular FIGS. 1a to 1c, an embodiment of a pump module 2 according to this invention comprises a housing 4 and a rotor 6 rotatably mounted in the housing. The rotor comprises a first axial extension 14 having a generally cylindrical shape and a second axial extension 16 also having a generally cylindrical shape. The first axial extension has a diameter D1 that is greater than a diameter D2 of the second axial extension. The housing 4 comprises a rotor housing portion 8 comprising a chamber 10, 12, within which the rotor is mounted, the rotor chamber comprising a first portion 10 for housing the first axial extension 14 and a second portion 12 for housing the second axial extension 16 of the rotor, the first portion having a larger diameter than the second portion. The housing further comprises an inlet channel 26 opening into the second chamber portion, configured to be connected to a liquid supply conduit or reservoir, and an outlet channel 28 for the pumped liquid to exit, opening into the first chamber portion. In the embodiments illustrated, both the inlet and outlet channels open transversely or radially into the chamber 10, 12 (as opposed to extending from axial ends of the chamber). Within the scope of the invention however, one of either the inlet channel or the outlet channel may extend from an axial end of the chamber.

Within the scope of the invention, the pump may be configured such that the inlet and outlet channels described herein are inversed, namely that the inlet opens into the larger diameter first chamber portion and the outlet opens into the smaller diameter second chamber portion. In other words, the pump may be configured to pump liquid from the large diameter portion towards the small diameter portion, or inversely may be configured to pump liquid from the small diameter portion towards the large diameter portion. For simplicity, only one of the variants is described in detail herein, however it is understood that using the same functioning principle, the pump may be configured according to the other variant.

The housing further comprises an inlet seal 20 surrounding the inlet channel 26 and mounted on a surface 29 of the chamber portion into which the inlet channel opens, and an outlet seal 18 surrounding the outlet channel 28 and mounted on a surface 27 of the chamber portion into which the outlet channel opens. The inlet seal 20 forms a closed circuit circumscribing the inlet 26 and the outlet seal 18 forms a closed circuit circumscribing the outlet 28. The outlet and inlet seals are configured to sealingly engage respective surfaces 31, 33 of corresponding first and second axial extensions of the rotor. The surface circumscribed by either the inlet or the outlet seal wraps around the corresponding rotor extension over an angle (α, β) that is preferably less than 180°.

Liquid supply channels 22, 24 are provided in the first and second axial extensions of the rotor.

According to an embodiment, as illustrated in FIGS. 1*a*-1*c*, the liquid supply channels 22, 24 may be in the form of depressions on the surface of the respective extensions, the depressions extending generally axially but at a slightly oblique angle with respect to the axial direction as defined by the direction of the axis of rotation of the rotor. The liquid supply channels may thus each wrap slightly around the respective rotor extension 14, 16 in a helical manner as illustrated. The configuration of the depressions—the non-abrupt dip and slight oblique angle—ensures an abrupt opening and closing of the valves to maximize the useful angle combined with a soft and smooth pump operation.

Figure 2:
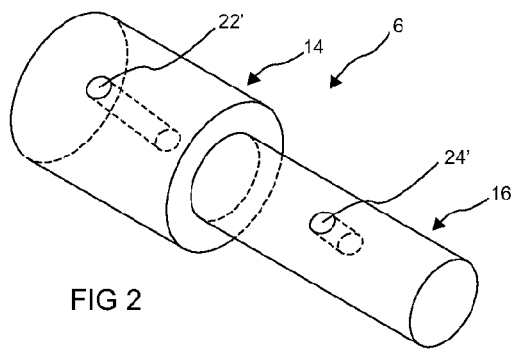
FIGS. 2 and 3 are perspective views of a rotor pump module according the variants of the invention.
Figure 3:
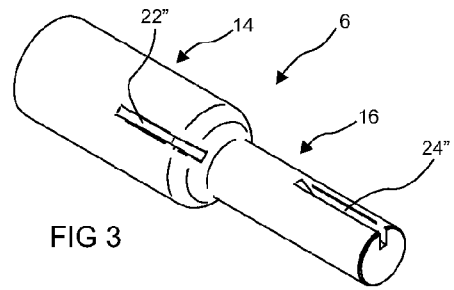

In another embodiment, as illustrated in FIG. 2, the liquid supply channels may be embedded within the rotor and have orifices (inlet, outlet) 22', 24' on the surfaces of the extensions. In yet another embodiment as illustrated in FIG. 3, the liquid supply channels may be in the form of axially extending grooves 22", 24" at the rotor surface. It is also possible to combine the features of the above two variants such that one of the liquid supply channels on one rotor extension is a depression or groove on the surface of the rotor and the other liquid supply channel on the other rotor extension is embedded within the rotor and has an outlet and an inlet opening onto the rotor surface.

The liquid supply channels 22, 24 and seals 18, 20, are configured to form an outlet valve V2 and an inlet valve V1 that open and close the outlet and inlet channels as a function of the rotor axial and angular position relative the housing. The inlet and outlet channels in the housing do not need to be aligned as illustrated but may be positioned relative to each other at any angle around the rotor, the liquid supply channels in the rotor extensions being positioned accordingly. It is understood that the shape, position and size of the seals and the shape, position and size of the liquid supply channels may vary considerably without departing from the scope of the invention, the essential function being to open and close the valves and to avoid both valves being open simultaneously.

The inlet and outlet seals 20, 18 may be formed as separate elements assembled in the housing, or as elements formed integrally with the housing, for instance injection molded in the housing. The seals may for instance be injected from silicone-based or thermoplastic elastomers or rubber in a two-component single injection molding process with the housing.

Sealing rings 41, 43 may be provided around first and second extensions of the rotor on outer sides of the inlet and outlet valves in order to seal the liquid filling part of the rotor chamber 23. These sealing rings may be in the form of O-ring seals or other seals mounted or injected in the housing or on the rotor.

The rotor 6 may be driven by any appropriate motor (not shown). For instance, the rotor may comprise a motor portion (not shown) with one or more permanent magnets providing one or more magnetic poles, driven in rotation by electromagnets in a motor stator portion (not shown). The motor stator portion may either be part of the pump, or part of a separate base unit into which the pump module is removably mounted. The base unit can be provided with electronics for controlling and operating the pump and/or for transmitting signals to a control unit via a wireless or wired link. The base unit may be configured as a reusable unit to which the pump module is removably mounted such that the pump module may be disposed of and replaced.

The axial displacement of the rotor may be performed by a magnetic or electromagnetic drive, or by a magnetic or spring biasing force combined with a cam system. A single sided cam system 35, 37 on the rotor 6 and housing 4 in conjunction with a spring or a magnetic biasing force BF is known per se in the prior art and illustrated in FIG. 6.

The axial displacement of the rotor may also be effected by means of a double-sided cam, according to an advantageous aspect of an embodiment of the invention, as illustrated in FIGS. 1*a* to 1*c*, 7, 8 and 10 to 12. In the double-sided cam variant, the rotor may be provided with a cam slot or grove 38, 38', 38" defining opposing cam surfaces 40*a*, 40*b*, 40*a'*, 40*b'*, 40*a"*, 40*b"*. A complementary cam finger 36 engaging in the cam slot or grove 38, 38', 38" is provided on the housing. The cam finger 36 may be rigidly attached to the housing, either integrally formed therewith or as a separate part assembled to the housing. In a variant, the cam finger may be elastically mounted in the housing such that it presses down into the rotor cam slot. An alternative variant (not shown) may comprise a cam finger on the rotor engaging in a cam slot provided in the housing to impart an axial movement on the rotor relative to the housing as a function of the angular movement of the rotor relative to the housing. For simplicity only the variant with a cam finger mounted on the housing engaging in a cam slot of the rotor will be described herein on the understanding that the cam elements may be inversed.

The cam slot may comprise a single slot extending fully around the rotor for the embodiment where the rotor rotates 360° for the pumping action (embodiment of FIGS. 4*a* to 4*f* and FIG. 10), or a two-portion slot extending only partially around the rotor for an oscillating rotational movement (embodiment of FIGS. 1*a*-1*c*, 8, 10-12).

The opposing cam surfaces 40*a*, 40*b*, 40*a'*, 40*b'*, 40*a"*, 40*b"* of the cam slot 38, 38', 38" may either define a slot of essentially constant width (FIG. 1*a*-1*c*, 11), or may define a cam slot of varying width (FIGS. 8, 10 and 12). The cam slot may thus either have opposing cam surfaces that conform to the cam finger as illustrated in FIG. 11, or in an advantageous variant, the cam slot may have opposed cam surfaces 40*a*, 40*b*, 40*a"*, 40*b"*, that are separated by a varying spacing that is configured to enable leakage or occlusion detection as will be described in more details further on in relation to FIGS. 9*a*-9*f*, 10 and 12.

In the embodiment with an oscillating rotor illustrated in FIGS. 4*a* to 4*f*, 11, 12 and FIGS. 1*a*-1*b*, the cam slot may comprise a first portion 39*a* corresponding to a first rotation direction, and a second portion 39*b* corresponding to a second rotation direction opposite to the first.

Figure 5A:
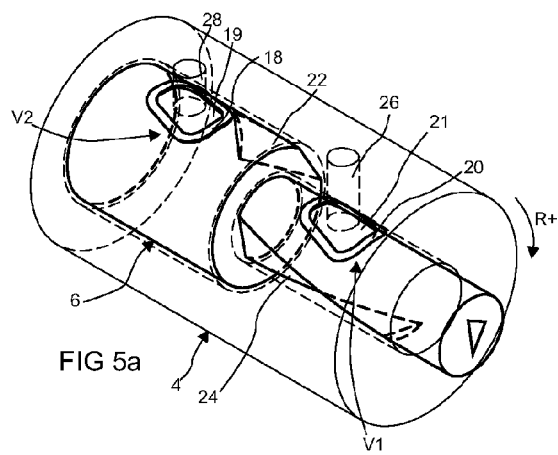
Figure 5B:
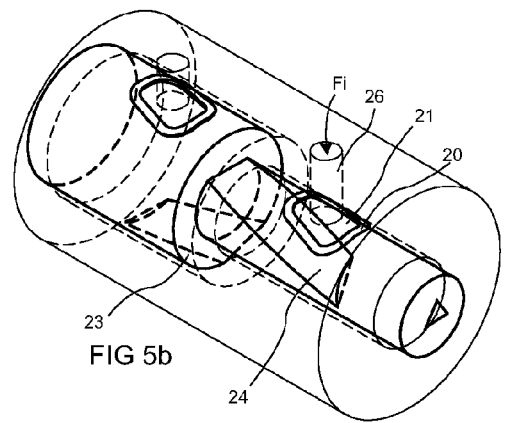
Figure 5C:
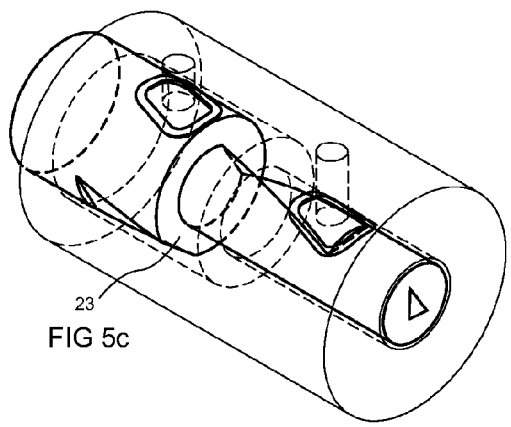
Figure 5D:
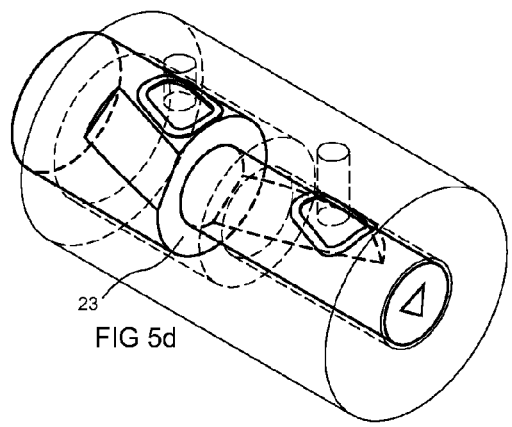
Figure 5E:
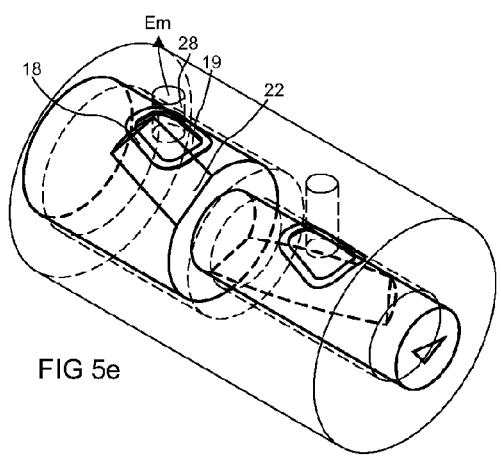
Figure 5F:
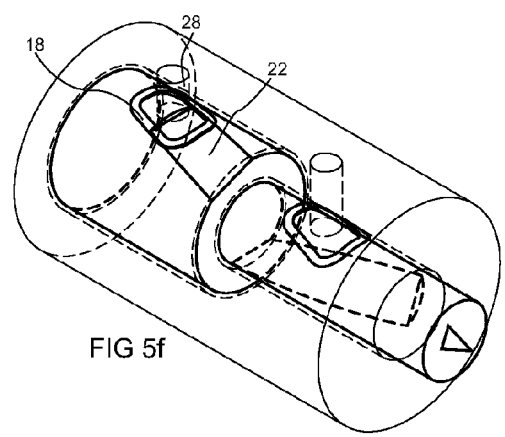

Referring now to FIGS. 5*a* to 5*f*, an embodiment of a pump module with a 360° rotating rotor is illustrated. The rotor rotates in a single direction R+ for the pumping action. In this embodiment the rotor may also rotate in the reverse direction in order to perform a reverse pumping operation, whereby in such a variant the axial displacement cam is configured to allow rotation in both directions. In FIG. 5*a*, the rotor is in a position corresponding to the valves V1 and V2 both in a closed position. The outlet valve V2 is formed by the outlet seal 18, outlet canal 28, first axial extension 14 and first liquid supply channel 22, whereas the inlet valve V1 is defined by the cooperation of the inlet seal 20, inlet canal 26, second axial extension 16 and second liquid supply channel 24. As may be seen, when the valves V1 and V2 are closed, the rotor is angularly and axially positioned such that neither of the liquid supply channels 22, 24 are found within the surface area 19, 21 circumscribed by the respective seals (hereinafter referred to as the "in-seal zones"). In these illustrations, the rotor shown is rotating in the clockwise direction, with the FIGS. 5a to 5f showing successive positions in a 360° pump cycle. In FIG. 5b, after a certain rotation, the inlet valve V1 opens when the liquid supply channel 24 enters into the inlet in-seal zone 21 circumscribed by the inlet seal 20. As the rotor turns and the inlet valve V1 opens, the rotor is also axially displaced such that the free volume 23 in the chamber increases and draws liquid Fi in through the inlet valve V2 to fill the chamber free volume 23. Outlet valve V2 is closed during the chamber filling process that continues as illustrated in FIG. 5c until the inlet valve V1 closes as illustrated in FIG. 5d, the outlet valve V2 being closed throughout the chamber filling process. Next, as illustrated in FIG. 5e, the outlet valve V2 opens when the liquid supply channel 22 engages in the outlet in-seal zone 19 circumscribed by the outlet seal 18. When the outlet valve V2 is open, the rotor axially displaces in the direction that reduces the chamber free volume 23 thus expelling liquid Em through the outlet canal 28, as also shown in FIG. 5f. The inlet valve V1 is closed throughout the chamber emptying process. The outlet valve V2 then closes as the rotor completes a 360° cycle to the position shown in FIG. 5a.

It may be noted that the rotor may be rotated in the reverse direction to pump liquid in the reverse direction (the inlet becomes the outlet and vice versa), the axial displacement cam being configured accordingly to allow rotation in both directions.

Figure 4A:
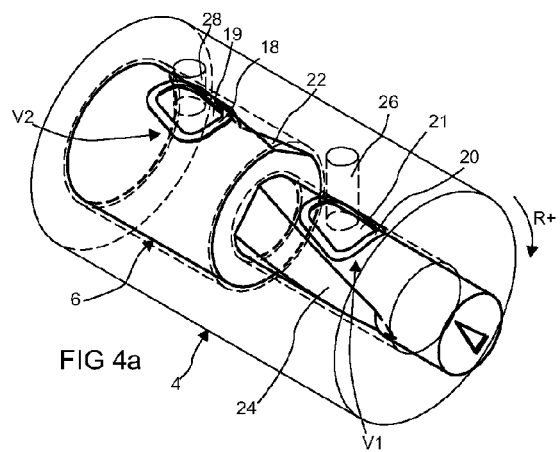
Figure 4B:
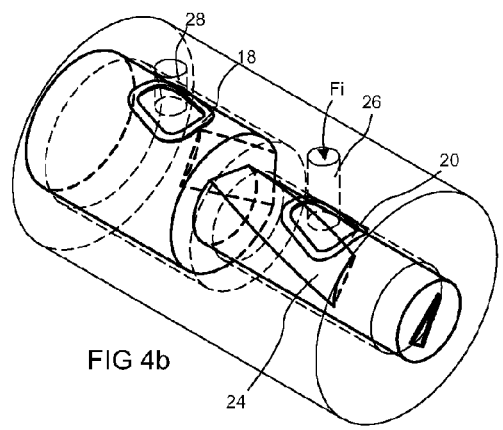
Figure 4C:
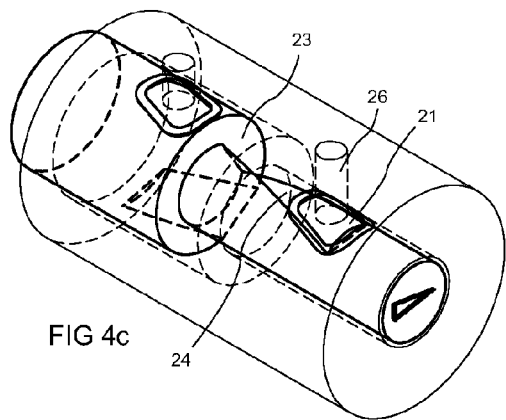
Figure 4D:
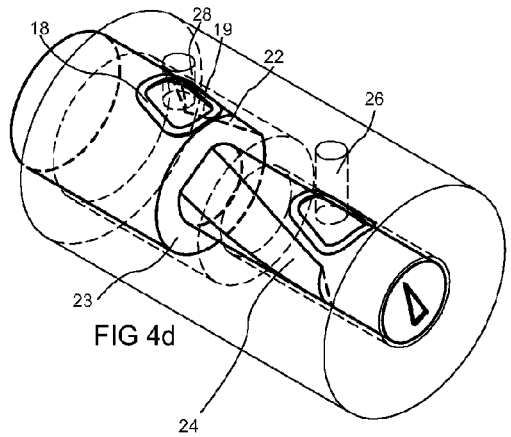
Figure 4E:
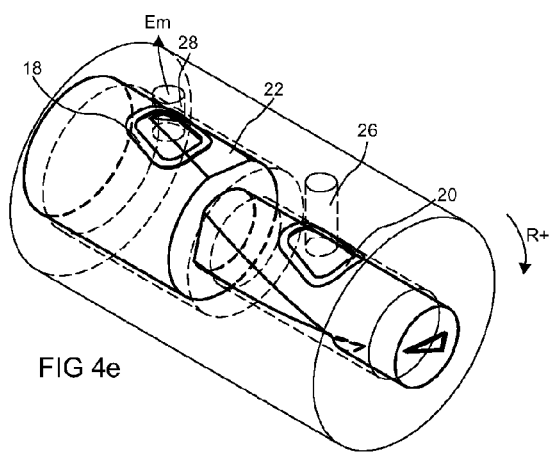
Figure 4F:
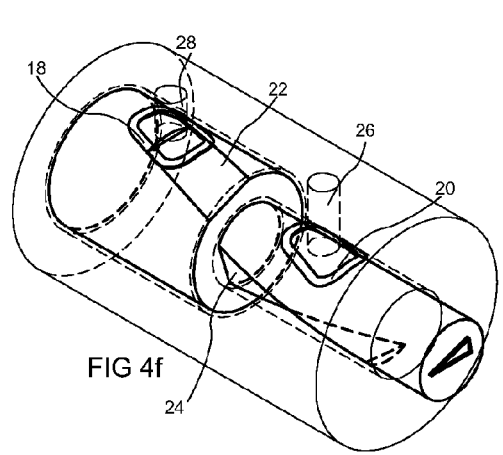

Referring to the embodiment of FIGS. 4a to 4f, an oscillating rotor is illustrated. In the position illustrated in FIG. 4a, both valves V1 are V2 are closed. The outlet valve V2 is formed by the outlet seal 18, outlet canal 28, first axial extension 14 and first liquid supply channel 22, whereas the inlet valve V1 is defined by the cooperation of the inlet seal 20, inlet canal 26, second axial extension 16 and second liquid supply channel 24. As may be seen, when the valves V1 and V2 are closed, the rotor is angularly and axially positioned such that neither of the liquid supply channels 22, 24 are found within the surface area 19, 21 circumscribed by the respective seals. In FIGS. 4a-4d illustrating the pump filling operation, the rotor shown is rotating in the clockwise direction R+, and in FIGS. 4d-4f illustrating the pump emptying operation, the rotor turns in the counterclockwise direction R−. In FIG. 4b, after a certain rotation from the closed valves position of FIG. 4a, the inlet valve V1 opens because the liquid supply channel 24 enters into the inlet in-seal zone 21 circumscribed by the inlet seal 20. As the rotor turns and the inlet valve V1 opens, the rotor is also axially displaced such that the free volume 23 in the chamber increases and draws liquid Fi in through the inlet valve V2 to fill the chamber free volume 23. Outlet valve V2 is closed during the chamber filling process that continues as illustrated in FIG. 4c until the inlet valve V1 closes as illustrated in FIG. 4d, the outlet valve V2 being closed throughout the chamber filling process. When both valves are closed as shown in FIG. 4d, the rotor stops and then rotates in the opposite direction R− (counterclockwise in this example) until the outlet valve V2 opens as illustrated in FIG. 4e, when the liquid supply channel 22 engages in the outlet in-seal zone 19 circumscribed by the outlet seal 18. When the outlet valve V2 is open, the rotor axially displaces in the direction that reduces the chamber free volume 23 thus expelling liquid Em through the outlet canal 28, as also shown in FIG. 4f. The inlet valve V1 is closed throughout the chamber emptying process up to the start position illustrated in FIG. 4a representing a full pumping cycle.

The axial movement of the oscillating pump illustrated in FIGS. 4a-4f is illustrated in the graphs of FIGS. 11 and 12. The cam path has a filling stage PF represented by half of the cam path and an emptying stage PE represented by the other half-section of cam path, the rotor positions shown in FIGS. 4a to 4f corresponding to the respective positions A to F indicated on the cam path. At the positions of change of rotation direction, as best illustrated in FIG. 7, the cam slot 38', 38" may comprise a step down 41 to define a point of no return ensure that the cam finger passes from one cam slot portion 39a to the next 39b, preventing the cam finger from returning along the same cam slot. In this variant, the cam finger 36 is movably mounted to the housing and biased against the rotor by a spring force or a magnetic force so that it tracks the bottom of the cam slot. The change in cam path from portion 39a to portion 39b and back to portion to 39a to commence a new oscillation pump cycle may also be effected without a step in the cam slot by application of an axial biasing force on the rotor at the rotor stop and change of direction positions, the biasing force at one position opposite the biasing force at the other position. The axial biasing force may be effected by an electromagnet or by an alternating spring system between the rotor and housing. Other means to ensure transition of the cam finger in the correct slot portion at the transition position may be employed within the scope of this invention, such as a pivoting or elastic arm in the slot that prevents return of the cam finger and ensures movement in only one sense.

Referring now to FIGS. 9a-9f, an embodiment of the invention with a 360° rotating rotor with leakage and occlusion detection will be described. The occlusion or leakage detection may be implemented in a variant with a single sided cam (as shown in FIG. 6) or a double sided cam with varying cam slot width as shown in FIG. 10. The axial displacement of the rotor depends on the profile of the cam and the opened and closed positions of the pump inlet and outlet valves V1, V2 as best illustrated in FIG. 9a where the profile of displacement of the rotor is in the present embodiment split into six sections S1, S2, S3a, S3b, S4 and S5. The rotor axial displacement may be detected or measured by a position sensor (not shown) such as a Hall effect sensor or optical sensor on the housing and/or rotor.

In section S1, no axial displacement takes place and the pump is neither filling nor emptying. Just before or as the cam protrusion on the housing meets the ramp CP2 of the rotor cam profile, the pump inlet valve V1 opens and the rotor is axially displaced along cam section S2 to draw liquid into the pump chamber up to the maximum axial displacement position defined by the cam portion CP3 after which the inlet valve closes and the rotor follows the flat path of section S3a along the cam portion CP3 until the cam finger on the housing moves past the cam profile section CP4. Along section S3b after the cam dropdown CP4, there is essentially no axial displacement since the liquid therein is essentially incompressible. There is however an inherent elasticity in the materials surrounding and containing the liquid in the pump, in particular in the seals which are elastic, such that there is a slight axial displacement step S3b as illustrated. Even though the cam profile abruptly changes at CP4 to the minimum value CP5 the rotor axial position does not change (except for the slight step) until the outlet valve opens allowing liquid to be expelled from the pump chamber.

In a variant of the invention where the cam ramp dropdown (CP4 to CP5) is essentially simultaneous with the valve V2 opening, occlusion detection is possible, however leakage detection is limited.

As the pump chamber empties, the axial displacement of the rotor follows the section S4 down to the minimum value defined by the cam profile CP5 to follow section S5 (which then rejoins S1 for further cycles). It should be noted that in order to keep the cam elements of the rotor and housing engaged, an axial biasing force is applied on the rotor relative to the housing. In typical embodiments, the axial biasing force may be applied magnetically and/or by means of a preloaded spring (not shown).

In the case of a leakage in the pump chamber, for example due to a defective seal, the rotor displacement may be detected since the rotor will displace axially in the zone Z1 before the outlet valve is opened and the ramp S4' as illustrated in FIG. 9b may be detected.

Leakage in the pump chamber may also be detected by effecting a back and forth displacement of the rotor after the ramp dropdown section CP4 in the section (zone Z1) where both valves V1 and V2 are closed as illustrated in FIG. 9f. The back and forth rotation of the rotor (also named herein "wobbling") while an axial force is applied to the rotor, over an angle of less than 180°, for instance between 10° to 60°, for instance 20° to 30°, causes the rotor shaft to effect an axial displacement S4 in a leakage condition of greater overall amplitude in the section where the valves are closed, compared to a configuration without wobbling (shown in FIG. 9b). Any leakage in the pump chamber can thus be more easily and reliably detected, especially leakage of small amplitude. The wobbling operation may be performed at the beginning, end or middle of an operation of the pump or even at every cycle of the rotor, depending on the pumping application. The wobbling operation is similar to a unidirectional rotational movement over a large angle (e.g. greater than 180°) to detect small amounts of leakage and a corresponding small axial displacement (e.g., less than $\frac{1}{10}^{th}$ of the total stroke). It can however be performed over a smaller angular region where both valves are closed and thus leave more angular space for the other functions, e.g. when open valves are required for intake or expel operations.

A back and forth rotation of the rotor while an axial force is applied to the rotor may also be effected to dislodge gas bubbles in the pump chamber, especially during the priming operation. Preferably, the wobbling is performed at a position where the cam finger is over the ramp section CP2, such that the rotor performs a rotational and axial back and forth movement to dislodge bubbles stuck to the pump chamber walls. In a variant, gas bubbles may be dislodged by rotating the rotor in a reverse direction until the cam finger hits the stop CP4 to create a mechanical shock (deceleration). A back and forth rotation may be effected two or more times with the housing cam hitting the stop CP4 at each reverse rotation to create a plurality of successive shocks to dislodge gas bubbles. The rotor may then effect one, two or more turns to evacuate the gas bubbles after the wobbling operation.

The bubble dislodging operation may be effected in the priming operation, but may also be effected at any time during the operation of the pump, at regular intervals or for example after a malfunction detection, in particular to distinguish between a malfunction due to leakage or the presence of gas in the pump. In effect, a rotor displacement according to FIG. 9b or 9f could represent gas in the pump chamber instead of leakage. In order to distinguish between these conditions, after detection of a presumed leakage malfunction, a bubble dislodging and evacuation operation is effected as described above, and thereafter a further leakage detection operation is effected. If the initial malfunction alarm was due to the presence of bubbles, then the bubbles will be evacuated during the bubble dislodging operation and the subsequent leakage detection test will signal normal operation. If the initial alarm was not due to the presence of gas in the pump, then the subsequent test should confirm the leakage malfunction.

As illustrated in FIG. 9c, if there is unusually low pressure downstream of the pump, for example because of a disconnected or leaking pipe downstream of the outlet (e.g. a disconnected catheter) the rotor will displace axially quicker towards the low position, and thus generate a steeper exhaust ramp S4" in zone Z2 when the outlet valve V2 is open. The reliable detection of leakage downstream of the pump will however depend on the pressure downstream of the pump and the pressure drop due to a leak downstream of the pump. The higher the pressure drop, the easier it will be to detect the leakage reliably. In applications where pumping occurs against a large relative pressure the leakage detection function downstream is thus particularly advantageous.

In the case of partial occlusion, for example in the case of impurities, a pinched outlet pipe, a blood clot and the like, the downstream pressure at the outlet will increase and cause the axial displacement S4''' of the rotor to be more gradual as illustrated in FIG. 9d as the axial biasing force will need to act against the backpressure. In the case of complete occlusion the pump rotor displacement S4'''', S5'''' may not reach the minimum position in zones Z3 when the outlet valve V2 is open, or by the time the outlet valve V2 closes again in zone Z4 as illustrated in FIG. 9e.

The occlusion and leakage detection methods described above may be applied in the same manner as described above in an embodiment with an oscillating pump as illustrated in FIGS. 8 and 12a-12e, whereby the equivalent cam portions CP1-CP5 and displacement sections S1-S5 are represented.

Each of the displacement profiles may be compared to an expected or defined reference profile S4, S5 as shown in FIGS. 9a and 12a that may be stored in a table of the measurement signal processing circuit of the pump. The reference profile may be for instance the cam profile CP1-CP2-CP3-CP4-CP5.

Referring to FIG. 10, a 360° cycle double sided cam is illustrated. The slot profile has a section that allows occlusion or leakage detection as described above. The axial displacement during pump filling is defined by the cam section CP3. Towards the end of the liquid expelling operation (i.e. when the outlet valve V2 is open), the opposite cam side 40b engages the cam finger 36 and the axial displacement during pump expelling is thus defined by the position of the cam section CP5'. The cam surfaces CP3 and CP5' thus act as reference surfaces that define an accurate amount of pumped liquid at each cycle, without depending on a high biasing force acting on the rotor as in the prior art systems. A weak biasing spring force configured for leakage, air-bubble or occlusion detection after closing of the inlet valve can be used, thus reducing the pressure in the pump chamber in operation zones Z1 and Z2 compared to the single sided cam variants which require a higher spring force in order to perform the liquid expelling function as well. The surface 43 opposed to the cam surface CP5' may form a dip to allow for some spacing tolerance with the cam surface CP5', since the latter acts as a reference surface.

The invention claimed is:

1. A pump comprising: a housing comprising a rotor chamber, inlet and outlet channels opening into the rotor chamber, and inlet and outlet seals mounted on a surface of the chamber, and a rotor rotatably and axially slidably received in the chamber and comprising a first axial extension comprising a liquid supply channel and a second axial extension comprising a liquid supply channel, the first and second axial extensions having different diameters, said inlet and outlet seals engaging a surface of the rotor, said liquid supply channel of each axial extension in conjunction with a corresponding said seal forming a valve that opens and closes as a function of the angular and axial displacement of the rotor, wherein at least one of the inlet and outlet channels opens radially into the rotor chamber, and wherein at least one of the inlet and outlet seals forms a closed circuit circumscribing said at least one of the inlet and outlet channels opening radially into the rotor chamber, and wherein a surface circumscribed by either the inlet or the outlet seal wraps around the corresponding rotor extension over an angle ($\alpha$, $\beta$) less than 360°.

2. The pump according to claim 1, wherein both inlet and outlet channels open radially into the rotor chamber and both inlet and outlet seals form a closed circuit circumscribing respective inlet and outlet channels.

3. The pump according to claim 1, wherein a surface circumscribed by either the inlet or the outlet seal wraps around the corresponding rotor extension over an angle ($\alpha$, $\beta$) less than 180°.

4. The pump according to claim 1, wherein the rotor is configured to oscillate over a rotation angle less than 360°, a back and forth movement constituting a pumping cycle.

5. The pump according to claim 1, wherein the rotor is configured to rotate in a single direction, a rotation angle of 360° constituting a pumping cycle.

6. The pump according to claim 1, wherein the rotor and housing comprise inter-engaging cam elements to effect the rotor axial displacement as a function of the rotation angle, said cam elements comprising a double sided cam slot.

7. The pump according to claim 6, wherein the double sided cam slot comprises a varying width configured to enable leakage or occlusion detection.

8. The pump according to claim 6, wherein the axial displacement during pump filling is defined by a cam section CP3 on one side of the cam slot, and the axial displacement during pump expelling is defined by a cam section CP5' on an opposite side of the cam slot, the cam surfaces CP3, CP5' acting as reference surfaces that define the volume of pumped liquid at each cycle.

9. The pump according to claim 6, wherein the cam slot comprises a first portion (39a) defining the axial displacement in one rotation direction, and a second portion (39b) defining the axial displacement in an opposite rotation direction.

10. The pump according to claim 9, wherein at a transition position in the cam slot corresponding to a change in direction of rotation, the cam slot comprises a step down configured to ensure that a cam finger progresses from one cam slot portion to the other cam slot portion.

11. A method of detecting occlusion or leakage of a pump, including:
providing a pump according to claim 1;
performing an initial measurement comprising turning the rotor in a forward pumping direction at least one revolution and storing the axial displacement as a function of rotation displacement profile in a look-up table as a cam profile; and
measuring the rotor axial displacement as a function of rotation displacement during subsequent pumping and comparing the measured rotor displacement with the stored cam profile.

12. The method according to claim 11, wherein before the cam profile setting, the rotor is rotated in a reverse direction until a cam shoulder (CP4) abuts a complementary cam finger, thus setting a defined reference starting position.

13. The method according to claim 11, wherein a back and forth displacement of the rotor is effected over an angle less than 90° when both valves V1 and V2 are closed to detect leakage.

* * * * *